(12) United States Patent
Drysdale (10) Patent No.: US 12,383,597 B1
(45) Date of Patent: *Aug. 12, 2025

(54) MEDICAL TREATMENT COMPOSITION, METHOD OF PREPARATION AND TREATMENT METHOD

(71) Applicant: Iracema Drysdale, Clearwater, FL (US)

(72) Inventor: Iracema Drysdale, Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/906,311

(22) Filed: Oct. 4, 2024

Related U.S. Application Data (63) Continuation-in-part of application No. 18/387,298, filed on Nov. 6, 2023, now Pat. No. 12,133,877.

(51) Int. Cl.
| | | |
|---|---|---|
| *A61K 36/00* | (2006.01) | |
| *A61K 36/61* | (2006.01) | |
| *A61K 36/8965* | (2006.01) | |
| *B01D 11/02* | (2006.01) | |

(52) U.S. Cl.
CPC .......... *A61K 36/8965* (2013.01); *A61K 36/61* (2013.01); *B01D 11/0288* (2013.01); *A61K 2236/15* (2013.01); *A61K 2236/33* (2013.01); *A61K 2236/331* (2013.01); *A61K 2236/333* (2013.01); *A61K 2236/53* (2013.01)

(58) Field of Classification Search
CPC ........................... A61K 36/61; A61K 36/8965
See application file for complete search history.

*Primary Examiner* — Qiuwen Mi
(74) *Attorney, Agent, or Firm* — John Rizvi; John Rizvi, P.A.—Patent Professor ®

(57) ABSTRACT

A medical treatment composition to treat one or more medical conditions, methods for preparation and treatment method are provided. The liquid composition comprises equal parts *Sansevieria* and ground/blended *Cloves*. The composition is capable of use in treating and curing cancer. A preparation method may comprise preparing a liquid *Sansevieria* component, preparing a liquid *Clove* component, adding the *Sansevieria* component to the *Clove* component, and permitting a resulting *Sansevieria* and ground *Clove* mixture to sit at room temperature for 24 hours, to provide a liquid medical treatment composition comprising by volume 50% of a *Sansevieria* component and 50% of a *Clove* component. Methods of treating cancer may include administering the composition.

6 Claims, 11 Drawing Sheets

PROVIDING REACTANTS OR COMPONENTS OF THE COMPOSITION BY:

(420A) PROVIDING A PREDETERMINED QUANTITY OF A SANSEVIERIA COMPONENT; AND
(420B) PROVIDING A PREDETERMINED QUANTITY OF A CLOVE COMPONENT;
SO THAT THE COMPONENTS ARE PRESENT IN THE PERCENT AGES BY VOLUME OF 50% SANSEVIERIA COMPONENT, AND 50% CLOVE COMPONENT

430

ADDING THE COMPONENTS TO A VESSEL BY:

(430A) PROVIDING A VESSEL OF SUFFICIENT VOLUME; AND
(430B) ADDING THE SANSEVIERIA AND CLOVE COMPONENTS TO THE VESSEL

440

FORMING THE COMPOSITION BY:

MIXING THE SANSEVIERIA AND CLOVE COMPONENTS IN THE VESSEL UNTIL THE COMPONENTS ARE COMPLETELY BLENDED TO PROVIDE A COMPOSITION COMPRISING A SANSEVIERIA AND CLOVE MIXTURE

450

PERMITTING THE COMPOSITION TO SIT AT ROOM TEMPERATURE FOR ABOUT 24 HOURS

FIG. 4

520A 520A-1
(520A-1a) PROVIDING 100g. OF SANSEVIERIA; AND
(520A-1b) PROVIDING 500mL. OF WATER 520A-2
PROVIDING A VESSEL OF SUFFICIENT VOLUME; AND ADDING THE 100g. OF SANSEVIERIA AND 500mL. OF WATER TO THE VESSEL 520A-3
FILTERING THE SANSEVIERIA AND WATER TO FORM A FILTERED SANSEVIERIA SOLUTION

620B-1
(620B-1a) PROVIDING 100g. OF CLOVES; AND
(620B-1b) PROVIDING 500mL. OF WATER

620B-2
GRINDING (BLENDING) THE 100g. OF CLOVES INTO A FINE GRIND (INTO SMALL SPECS) (SO THE CLOVES ARE GROUND AND NOT POWDERED)

620B-3
PROVIDING A VESSEL OF SUFFICIENT VOLUME AND PREPARING AN UNFILTERED CLOVE SOLUTION BY ADDING THE 100 g. OF GROUND CLOVES TO 500 mL OF WATER AT ROOM TEMPERATURE TO PROVIDE AN UNFILTERED CLOVE SOLUTION

720B-1
(720B-1a) PROVIDING 100g. OF CLOVES; AND
(720B-1b) PROVIDING 500mL. OF 91% ALCOHOL

720B-2
GRINDING (BLENDING) THE 100g. OF CLOVES INTO A FINE GRIND (INTO SMALL SPECS) (SO THE CLOVES ARE GROUND AND NOT POWDERED)

720B-3
PROVIDING A VESSEL OF SUFFICIENT VOLUME AND PREPARING AN UNFILTERED CLOVE SOLUTION BY ADDING THE 100 g. OF GROUND CLOVES TO 500 mL OF 91% ALCOHOL TO PROVIDE AN UNFILTERED CLOVE SOLUTION

820
PROVIDING REACTANTS OR COMPONENTS OF THE COMPOSITION BY:

(820A) PROVIDING A PREDETERMINED QUANTITY OF A SANSEVIERIA COMPONENT; AND
(820B) PROVIDING A PREDETERMINED QUANTITY OF A CLOVE COMPONENT; SO THAT THE COMPONENTS ARE PRESENT IN THE PERCENTAGES BY VOLUME OF 50% SANSEVIERIA COMPONENT, AND 50% CLOVE COMPONENT

830
ADDING THE COMPONENTS TO A VESSEL BY:

(830A) PROVIDING A VESSEL OF SUFFICIENT VOLUME; AND
(830B) ADDING THE SANSEVIERIA AND CLOVE COMPONENTS TO THE VESSEL

840
FORMING THE COMPOSITION BY

MIXING THE SANSEVIERIA AND CLOVE COMPONENTS IN THE VESSEL UNTIL THE COMPONENTS ARE COMPLETELY BLENDED TO PROVIDE A COMPOSITION COMPRISING A SANSEVIERIA AND CLOVE MIXTURE

850
PERMITTING THE COMPOSITION TO SIT AT ROOM TEMPERATURE FOR ABOUT 24 HOURS

860
PROVIDING A SUITABLE BOTTLE OR CONTAINER WITH A REMOVABLE CAP OR COVER

870
REMOVING THE CAP OR COVER FROM THE BOTTLE OR CONTAINER, ADDING THE COMPOSITION TO THE BOTTLE OR CONTAINER, AND REPLACING THE CAP OR COVER ON THE BOTTLE OR CONTAINER

1120
PROVIDING REACTANTS OR COMPONENTS OF THE COMPOSITION CONCENTRATE BY:

(1120A) PROVIDING A PREDETERMINED QUANTITY OF A SANSEVIERIA COMPONENT; AND
(1120B) PROVIDING A PREDETERMINED QUANTITY OF A CLOVE COMPONENT

1130
ADDING COMPONENTS TO A VESSEL BY:

(1130A) PROVIDING A VESSEL OF SUFFICIENT VOLUME; AND
(1130B) ADDING THE SANSEVIERIA COMPONENT, AND THE CLOVE COMPONENT TO THE VESSEL

1140
FORMING THE COMPOSITION CONCENTRATE BY:

MIXING THE COMPONENTS IN THE VESSEL UNTIL THE COMPONENTS ARE COMPLETELY BLENDED TO PROVIDE THE COMPOSITION CONCENTRATE

FIG. 11

MEDICAL TREATMENT COMPOSITION, METHOD OF PREPARATION AND TREATMENT METHOD

CROSS-REFERENCE TO RELATED APPLICATIONS

This application is a Continuation-In-Part under 35 U.S.C. § 120 of the U.S. patent application Ser. No. 18/387,298 filed on Nov. 7, 2023, which is incorporated by reference herein in its entirety.

FIELD OF THE INVENTION

The present invention relates generally to medical treatment compositions, and more particularly to a medical treatment composition, a method for its preparation, and a method for medical treatment by administering the composition.

BACKGROUND OF THE INVENTION

Cancer treatments are the subject of extensive research and development. In spite of much focus and monetary investment on the part of pharmaceutical and biotechnology companies, it appears that no cure for cancer has yet been developed. Treatments exist which require a weighing of the treatment risk against the potential benefits the receiving the treatments.

Options appear to include natural pharmaceutical compositions, which have not resulted in an effective treatment or a cure.

For example, one option appears to pertain to a natural pharmaceutical composition, a preparation method thereof and application thereof in preparation of toxicity reducing and efficacy enhancing drugs for cancer chemotherapy. The natural pharmaceutical composition consists of a decoction concentrated extract of *Andrographis paniculata* (Burm.f.) Nees and *Piper longum* I., andrographolide, an ethanol extract of *Piper longum* I. and piperine which are in the ratio of (2-3):(6-9):(5-8):(1-5). The composition is alleged to provide an excellent treatment effect on cancer-chemotherapy-related diarrhea and can simultaneously play a synergic role in cancer chemotherapy. The option has not resulted in a cure, and has not been adopted for widespread use.

Another option appears to pertain to a natural drug extract. Said natural drug extract consists of an extract prepared by decocting and concentrating common andrographis herb and *Clove* in water, common andrographis herb lactone extract, *Clove* ethanol extract and eugenol by a ratio of (4-6):(3-6):(2-4):(6-9). The composition is alleged to have an extremely good treatment effect on diarrhea related with cancer chemotherapy and also has a synergism effect on cancer chemotherapy. The option has not resulted in a cure, and has not been adopted for widespread use.

Yet another option appears to pertain to a natural medicine composition and a preparation method thereof. The natural medicine composition is composed of an extract from *Fructus schisandrae chinensis* and *Cloves* by decoction with water and concentration, *Fructus schisandrae chinensis* polysaccharides, an extract from *Cloves* with ethyl alcohol, and eugenol according to the ratio of (2-4) to (3-5) to (3-8) to (5-8). The composition alleges to have a curative effect on cancer chemotherapy induced diarrhea. However, the option has not resulted in a cure, and has not been adopted for widespread use.

A method exists for preparing a potential herbal anti-cancer medicine from the leaves and twigs of *Calotropis gigantean* for prevention and treatment of all types of cancers, using fresh extract of leaves and twigs of *Calotropis gigantea* fortified with unrefined sugarcane sugar (jaggery). The method includes dessicating an aqueous extract of leaves and twigs of *Calotropis gigantea*. A [3H]-Thymidine growth assay was performed against cancer cell lines, WM 902-B and WM1341-D. The extract [28 mgms] was dissolved in 2 ml control at 0.5%, 0.1% DMSO. The extract is alleged to be highly inhibitory at all dilutions to and highly inhibitory to cancer cell lines cancer cell lines, WM 902-B and WM1341-D. However, the option has not resulted in a cure, and has not been adopted for widespread use.

Accordingly, there remains a need for a solution to the problem of cancer treatment and cure.

SUMMARY OF THE INVENTION

The present invention is directed to a medical treatment compositions for treating and curing cancer, to a method for its preparation, and a method for providing cancer treatment by administering the composition.

In a one implementation of the invention, a composition for cancer prevention and treatment comprises *Sansevieria* and *Cloves*. The present invention is capable of preventing and healing cancer.

According to the website Garden-Care.org.UK, in addition to aesthetic features, *Sansevieria* plants may beneficially filter indoor air; remove toxic pollutants; combat airborne allergens; combat minor ailments; help boost mental health; be easily cared for; and help enhance the "energy" of a space, according to feng shui. 7 *Benefits Of Keeping Snake Plants In Your Home*; https://garden-care.org.uk/health-wellbeing/7-benefits-of-keeping-snake-plants-in-your-home/. Moreover, certain species are recognized by NASA as being capable of purifying air by removing some pollutants such as formaldehyde, xylene, and toluene. Wolverton, B. C.; Johnson, Anne; Bounds, Keith (15 Sep. 1989). "*Interior Landscape Plants for Indoor Air Pollution Abatement*" (PDF). NASA.

It is commonly known that *Sansevieria* plants are recognized to be toxic if ingested.

*Clove* essential oil may be used to inhibit mold growth on some foods. *Cloves* are used in traditional medicine as the essential oil, which is used as an analgesic for dental emergencies. There is evidence that *Clove* oil containing eugenol is effective for toothache pain and other types of pain, and one review reported efficacy of eugenol combined with zinc oxide as an analgesic for alveolar osteitis. *Clove* essential oil may prevent the growth of *Enterococcus faecalis* bacteria which is often present in a root canal treatment failure.

The potential use of *Clove* and *Sansevieria* for cancer prevention and anticancer treatments is antithetical to present teachings. The present invention provides an unprecedented solution to these important problems, is able to be used to prevent cancer, and to heal and improve the quality of life for people who have been diagnosed with cancer.

The mechanism by which these components may prevent and heal cancer appears to be related to the synergistic composition of the present invention.

In one aspect, the present invention provides a liquid composition comprising a predetermined amount of *Sansevieria* and a predetermined amount of *Cloves*.

In one aspect, the present invention provides a liquid composition comprising equal parts *Sansevieria* and blended *Cloves*.

In one aspect, the present invention provides a liquid composition comprising by volume 50% of a *Sansevieria* component and 50% of a *Clove* component.

In one aspect the present invention provides a liquid composition comprising 100 g. of *Sansevieria* and 100 g. of blended *Cloves*.

In another implementation, the present invention provides a method of preparing a medical treatment composition, the method comprising:
- providing 100 g. of *Sansevieria*;
- providing 100 g. of *Cloves*;
- preparing a filtered *Sansevieria* solution by adding the 100 g. of *Sansevieria* to 500 ml of water, and filtering the resulting mixture;
- grinding (blending) the 100 g. of *Cloves* into a fine grind (into small specks) (the *Cloves* are ground, not powdered);
- preparing an unfiltered *Clove* solution by adding to the 100 g. of ground *Cloves* 500 ml of water at room temperature, or by providing 500 ml of 91% alcohol and adding the 500 ml of 91% alcohol to the 100 g. of ground *Cloves* instead of water;
- preparing a *Sansevieria* and ground *Clove* mixture by adding to the *Clove* solution the filtered *Sansevieria* solution;
- blending the *Sansevieria* and ground *Clove* mixture until the composition is provided; and
- permitting the *Sansevieria* and ground *Clove* mixture to sit at room temperature for 24 hours.

In one aspect, the method may further comprise providing a container or bottle with a cap or cover, removing the cap or cover from the container or bottle, adding the medical treatment composition to the container or bottle and replacing the cap or cover. In a further aspect, the composition may be stored at room temperature. In another aspect, the composition may be stored refrigerated. In a still further aspect, at least one dosage of the composition may be stored refrigerated.

In an additional implementation, the present invention provides a method for treating a medical condition, comprising:
- providing a medical treatment composition comprising a mixture of *Sansevieria* and ground *Clove* as disclosed herein; and
- administering the medical treatment composition by taking one (1) tablespoon (tbsp.) after breakfast, after lunch and after dinner, followed by two (2) tablespoons (tbsp.) of an antacid composition.

In one aspect, the present invention provides a method for preventing or treating a medical condition comprising:
- providing a liquid composition comprising *Sansevieria* and blended *Cloves*; and
- administering the liquid composition.

In one aspect, administering the liquid composition comprises ingesting a predetermined quantity of the liquid composition daily.

In one aspect, the medical condition comprises cancer.

In another aspect, the medical condition may be one of at least a fungal infection, arthritis, toothache, or acne.

In one aspect, the present invention provides a method of preventing or treating a medical condition wherein the liquid composition comprises equal parts *Sansevieria* and blended *Cloves*.

In one aspect, the present invention provides a method of preventing or treating a medical condition wherein the liquid composition comprises by volume 50% of a *Sansevieria* component and 50% of a *Clove* component.

In one aspect, the present invention provides a method of preventing or treating a medical condition wherein the liquid composition comprises 100 g. *Sansevieria* and 100 g. blended *Cloves*.

In another aspect, the medical disease may be any currently known or newly identified medical disease or condition.

In a further aspect, the medical disease or condition is cancer.

In one aspect, the method further comprises precluding use of the composition by pregnant women, or by women during their menstrual cycle, as the composition may cause hemorrhaging.

In one aspect, the method for preventing or treating a cancer further comprises administering the liquid composition with another supplemental medical treatment. In a further aspect, the supplemental medical treatment comprises a pharmaceutical drug. In a still further aspect, the supplemental medical treatment comprises chemotherapy. In a yet further aspect, the supplemental medical treatment comprises radiation.

In one aspect, the method further comprises administering the medical having cancer radiation treatments at the discretion of a primary physician.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 9. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is directed to medical treatment compositions for treating and curing cancer. Shown throughout the figures, the present invention is further directed to methods for preparing the medical treatment compositions and for providing cancer treatment by administering the compositions.

In a first implementation, the present invention provides a medical treatment composition which comprises *Sansevieria* and *Cloves*. The composition may comprise a liquid composition further comprising a predetermined amount of *Sansevieria* and a predetermined amount of *Cloves*. In some embodiments, the liquid composition comprises equal parts *Sansevieria* and blended *Cloves*.

The liquid composition may comprise by volume 50% of a *Sansevieria* component and 50% of a *Clove* component.

In some embodiments, the present invention provides a liquid composition comprising 100 g. of *Sansevieria* and 100 g. of blended *Cloves*.

The medical treatment composition may be prepared by a method including one or more of the following steps and combinations thereof.

providing 100 g. of *Sansevieria*;
providing 100 g. of *Cloves*;
preparing a *Sansevieria* component comprising a filtered *Sansevieria* solution by adding the 100 g. of *Sansevieria* to 500 ml of water, and filtering the resulting mixture;
preparing a *Clove* component comprising an unfiltered *Clove* solution by grinding (blending) the 100 g. of *Cloves* into a fine grind (into small specks) (the *Cloves* are ground, not powdered); and
preparing the unfiltered *Clove* solution by providing 500 mL of a solvent selected from water at room temperature, 91% alcohol, and combinations thereof; and adding to the 100 g. of ground *Cloves* 500 mL of the solvent;
preparing a *Sansevieria* and ground *Clove* mixture by adding to the *Clove* component (which comprises the *Clove* solution) the *Sansevieria* component (which comprises the filtered *Sansevieria* solution); and
permitting the *Sansevieria* and ground *Clove* mixture to sit at room temperature for 24 hours.

The methods of preparing the medical treatment composition may comprise providing components in the same proportions. Nonlimiting examples include providing 50 g. of *Sansevieria* and 250 mL of water; 50 g. of *Clove*, and 250 mL of solvent; or providing 200 g. of *Sansevieria* and 1000 mL of water, 200 g. of *Clove*, and 1000 mL of solvent.

The method may further comprise providing a container or bottle with a cap or cover, removing the cap or cover from the container or bottle, adding the medical treatment composition to the container or bottle and replacing the cap or cover.

The composition may be stored at room temperature. Alternatively, the composition may be stored refrigerated.

Further, the composition may be stored refrigerated in at least one dosage. For example without limitation, the at least one dosage may be stored refrigerated in at least one container, such as at least one recloseable or resealable container, or at least one sealed container.

Referring to FIGS. 1-8, in a second implementation, methods are presented for preparing medical treatment compositions for treating and curing cancer, the compositions comprising *Sansevieria* and *Cloves*.

Figure 1:
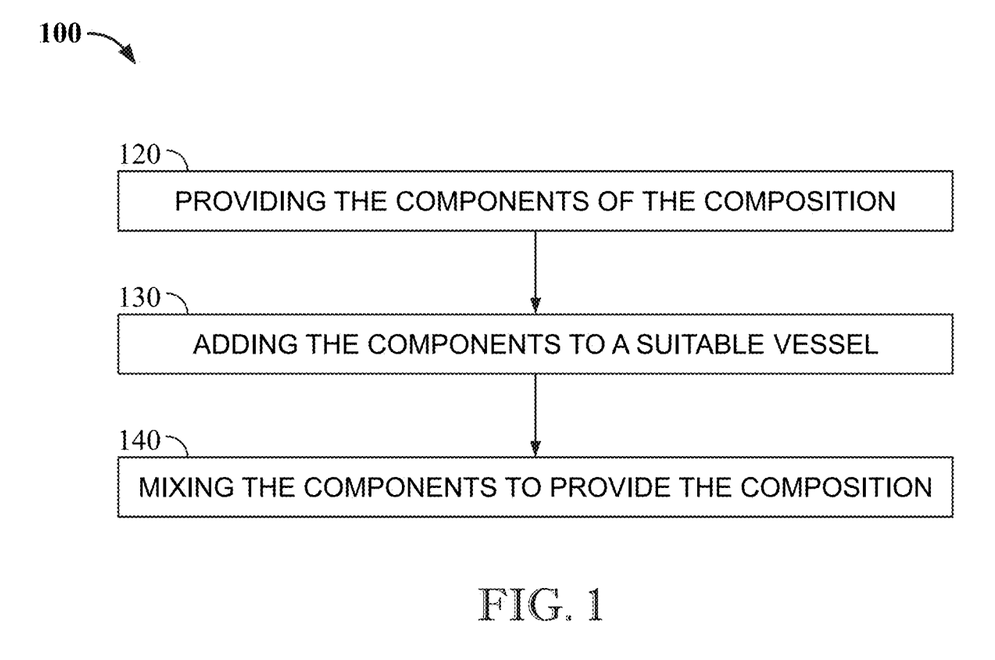
FIG. 1 presents a flow chart of a method in accordance with an illustrative embodiment of the present invention.

Referring to FIG. 1, a method 100 for preparing a composition in accordance with the present invention comprises:
 (120) providing the components of the composition;
 (130) adding the components to a suitable vessel; and
 (140) mixing the components to provide the composition.

Figure 2:
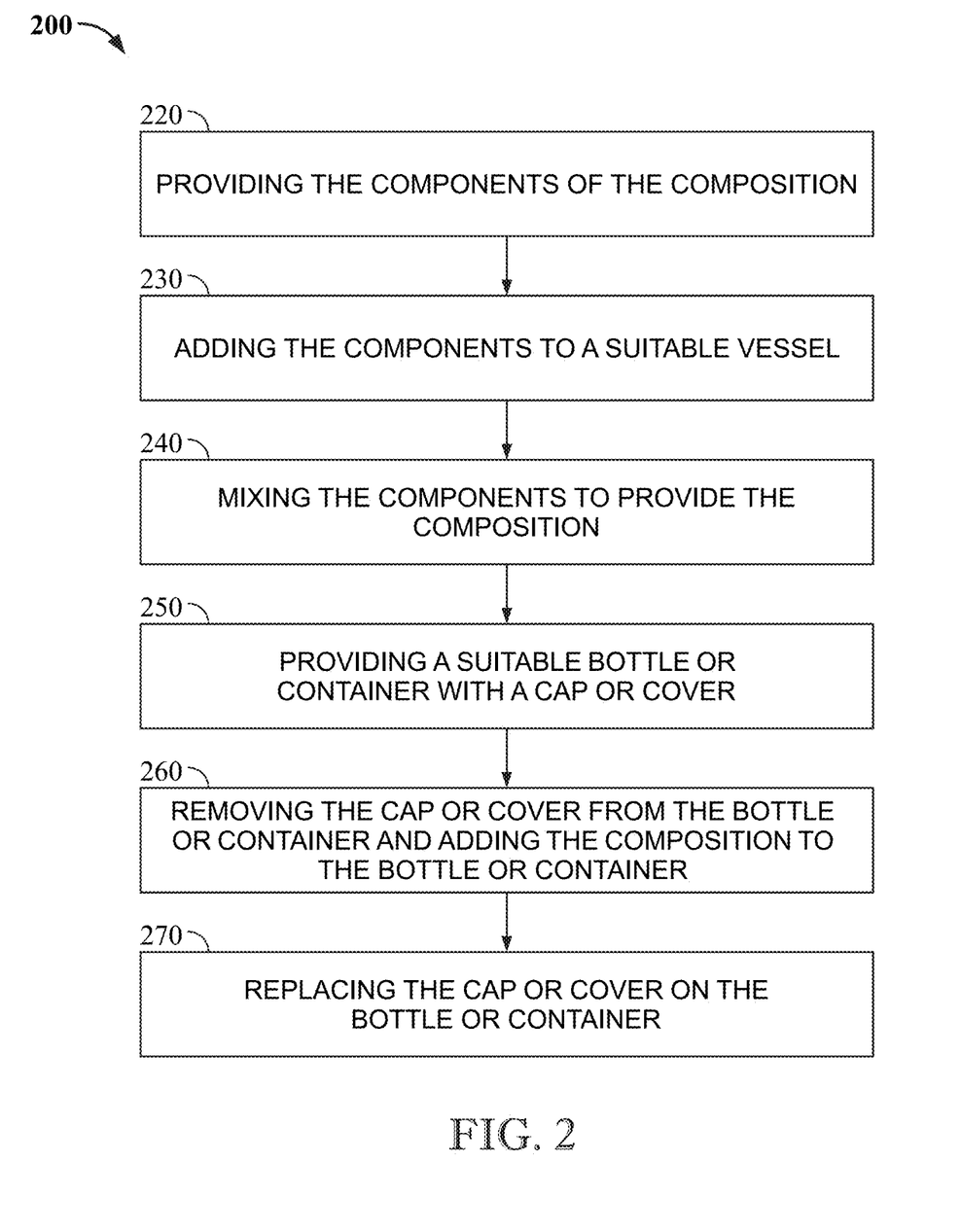
FIG. 2 presents a flow chart of a method in accordance with an illustrative embodiment of the present invention.

Referring to FIG. 2, a method 200 for preparing a composition in accordance with the present invention may further comprise:
 (220) providing the components of the composition;
 (230) adding the components to a suitable vessel;
 (240) mixing the components to provide the composition;
 (250) providing a suitable bottle or container with a cap or cover;
 (260) removing the cap or cover from the bottle or container and adding the composition to the bottle or container; and
 (270) replacing the cap or cover on the bottle or container.

Figure 3:
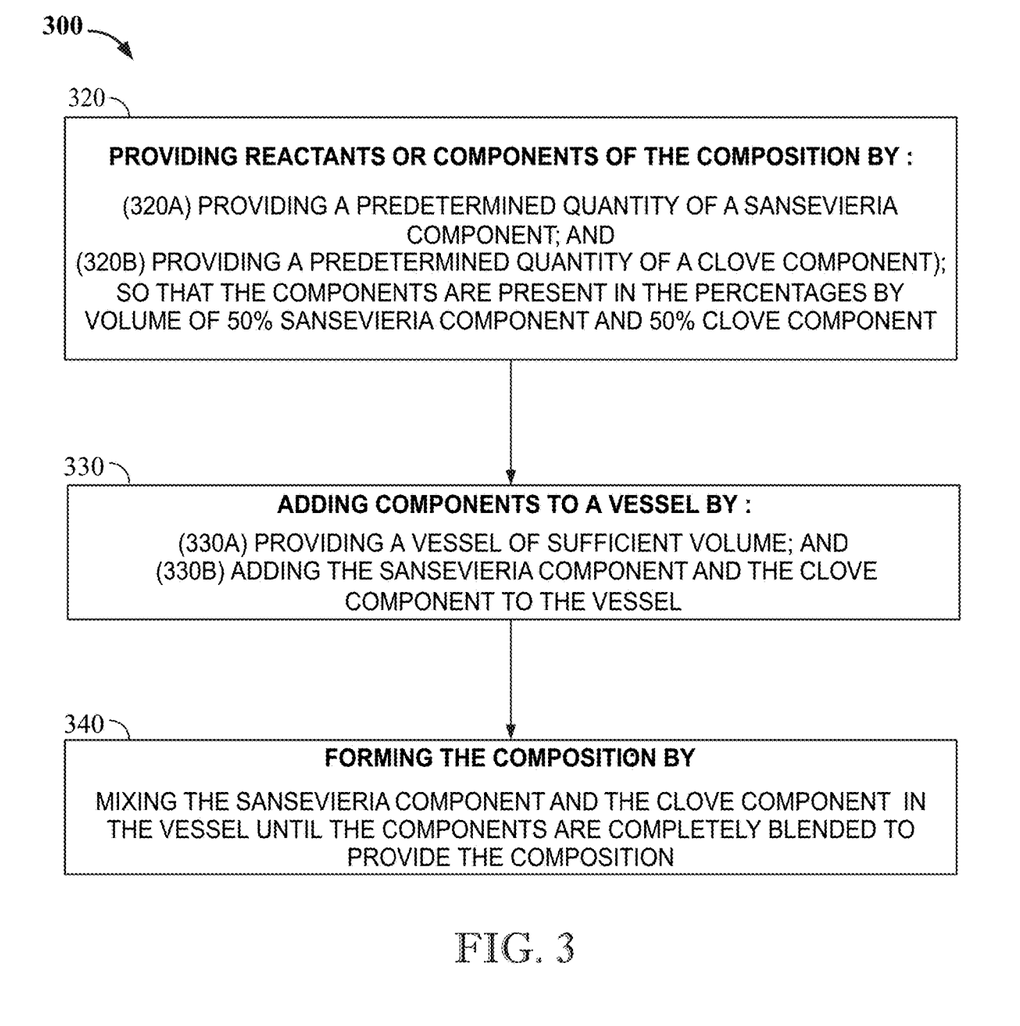
FIG. 3 presents a flow chart of a method in accordance with an illustrative embodiment of the present invention.

Referring now to FIG. 3, a method 300 in accordance with the present invention may comprise:
 (320) Providing reactants or components of the composition by:
 (320a) providing a predetermined quantity of a *Sansevieria* component; and
 (320b) providing a predetermined quantity of a *Clove* component);
 so that the components are present in the percentages by volume of 50% *Sansevieria* component and 50% *Clove* component;
 (330) Adding components to a vessel by:
 (330a) providing a vessel of sufficient volume; and
 (330b) adding the *Sansevieria* component and the *Clove* component to the vessel; and
 (340) Forming the composition by mixing the *Sansevieria* component and the *Clove* component in the vessel until the components are completely blended to provide the composition.

Figure 4:
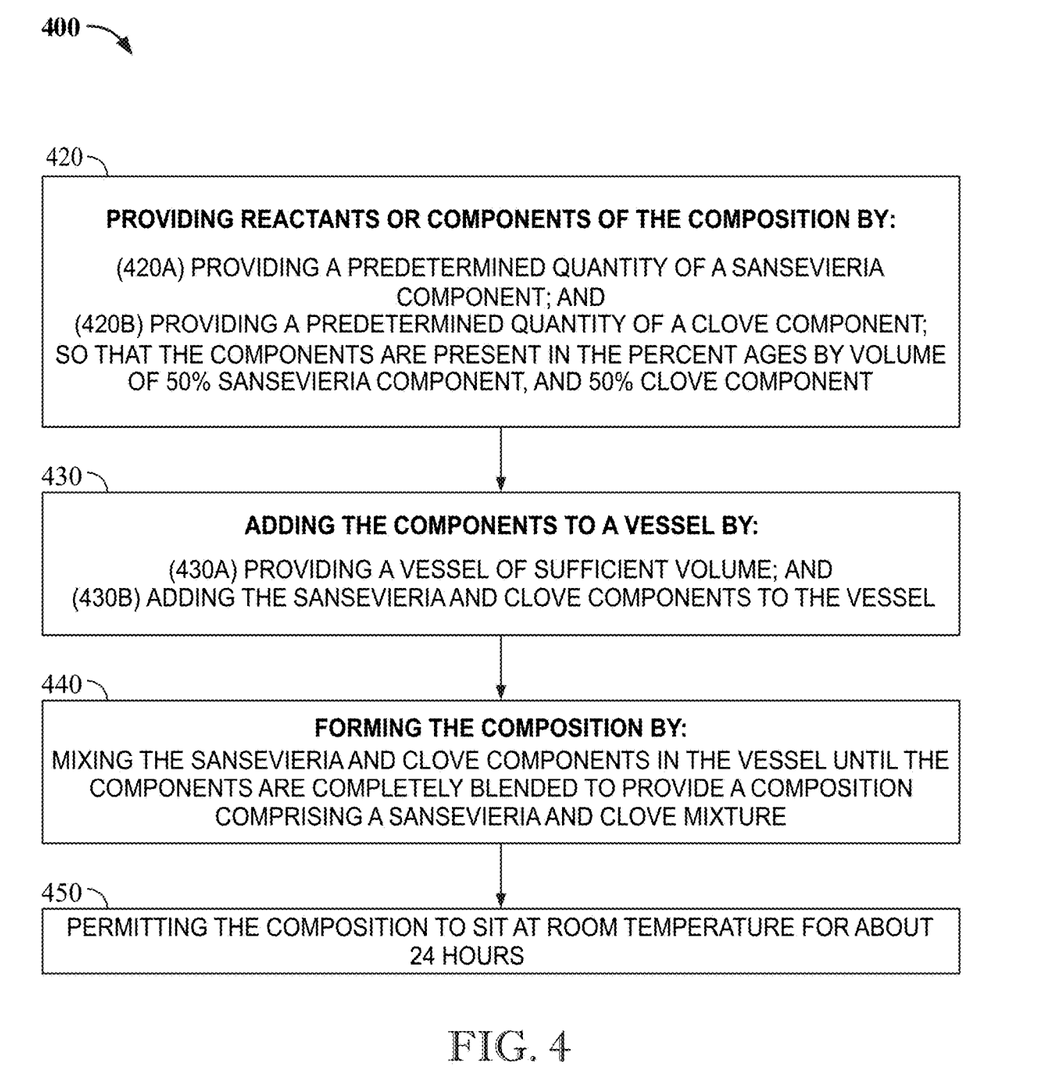
FIG. 4 presents a flow chart of a method in accordance with an illustrative embodiment of the present invention.

Referring now to FIG. 4, a method 400 may further comprise:
 (420) Providing reactants or components of the composition by:
 (420a) providing a predetermined quantity of a *Sansevieria* component; and
 (420b) providing a predetermined quantity of a *Clove* component;

so that the components are present in the percentages by volume of 50% *Sansevieria* component, and 50% *Clove* component;
(430) Adding the components to a vessel by:
  (430a) providing a vessel of sufficient volume; and
  (430b) adding the *Sansevieria* and *Clove* components to the vessel;
(440) Forming the composition by mixing the *Sansevieria* and *Clove* components in the vessel until the components are completely blended to provide a composition comprising a *Sansevieria* and *Clove* mixture; and
(450) permitting the composition to sit at room temperature for about 24 hours.

Figure 5:
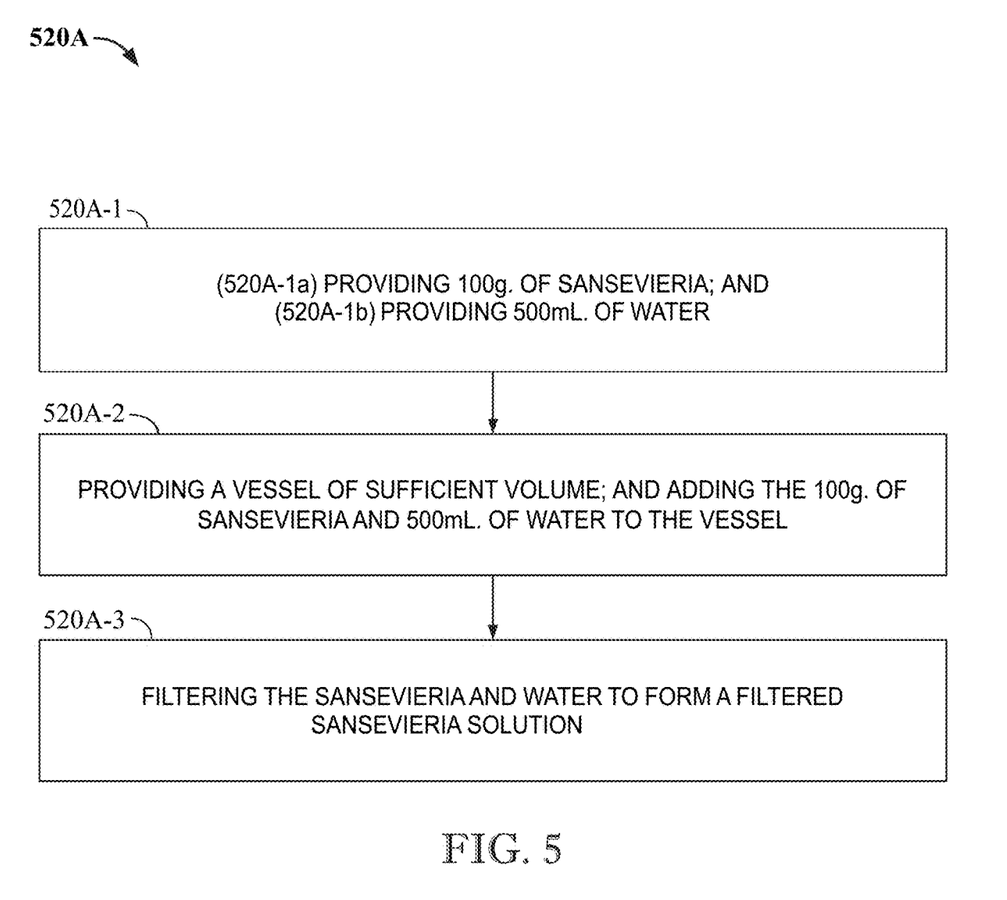
FIG. 5 presents a flow chart of a method in accordance with an illustrative embodiment of the present invention.

Referring now to FIG. 5, a method (520A-1) for providing a *Sansevieria* component may comprise:
  (520A-1a) providing 100 g. of *Sansevieria*; and
  (520A-1b) providing 500 mL. of water;
  (520A-2) providing a vessel of sufficient volume and adding the 100 g. of *Sansevieria* and the 500 mL of water to the vessel; and
  (520A-3) filtering the *Sansevieria* and water to form a filtered *Sansevieria* solution.

Figure 6:
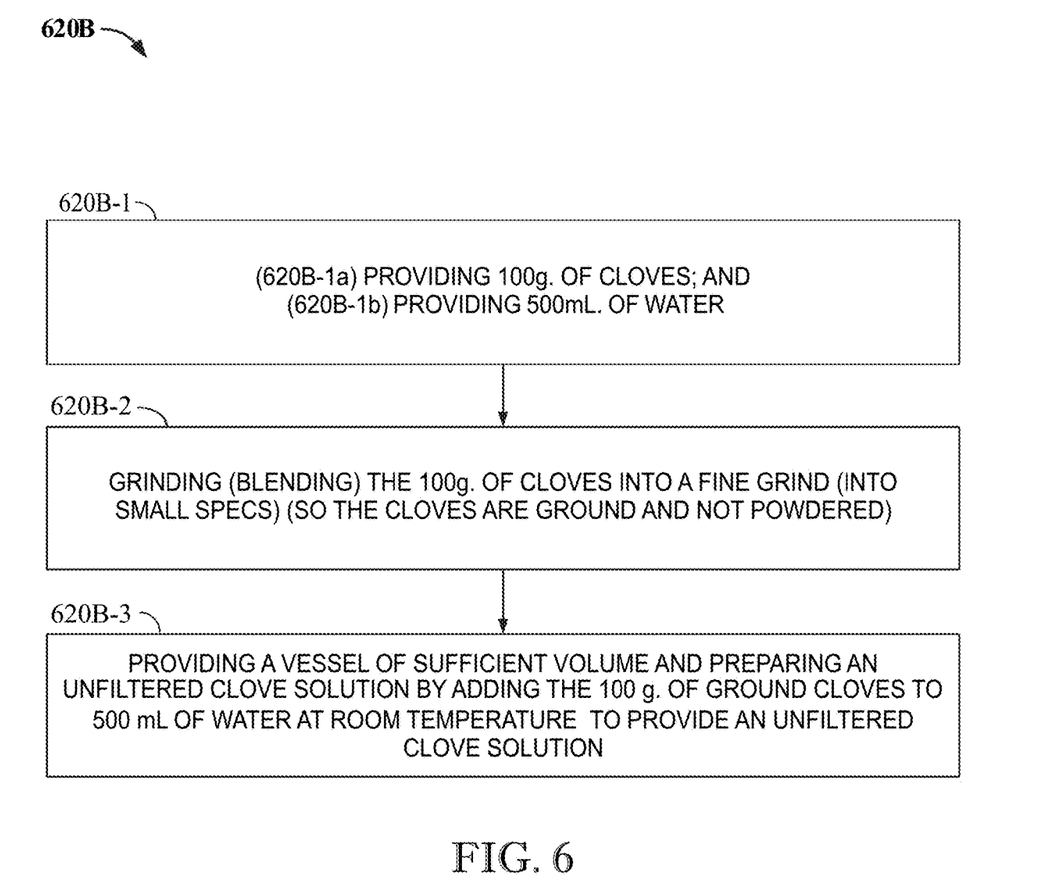
FIG. 6 presents a flow chart of a method in accordance with an illustrative embodiment of the present invention.

Referring now to FIG. 6, a method (620B) for providing a *Clove* component may comprise:
  (620B-1a) providing 100 g. of *Cloves*; and
  (620B-1b) providing 500 mL. of water;
  (620B-2) grinding (blending) the 100 g. of *Cloves* into a fine grind (into all specs) (so the *Cloves* are ground and not powdered); and
  (620B-3) providing a vessel of sufficient volume and preparing an unfiltered *Clove* solution by adding the 100 g. of ground *Cloves* to 500 mL of water at room temperature to provide an unfiltered *Clove* solution.

Figure 7:
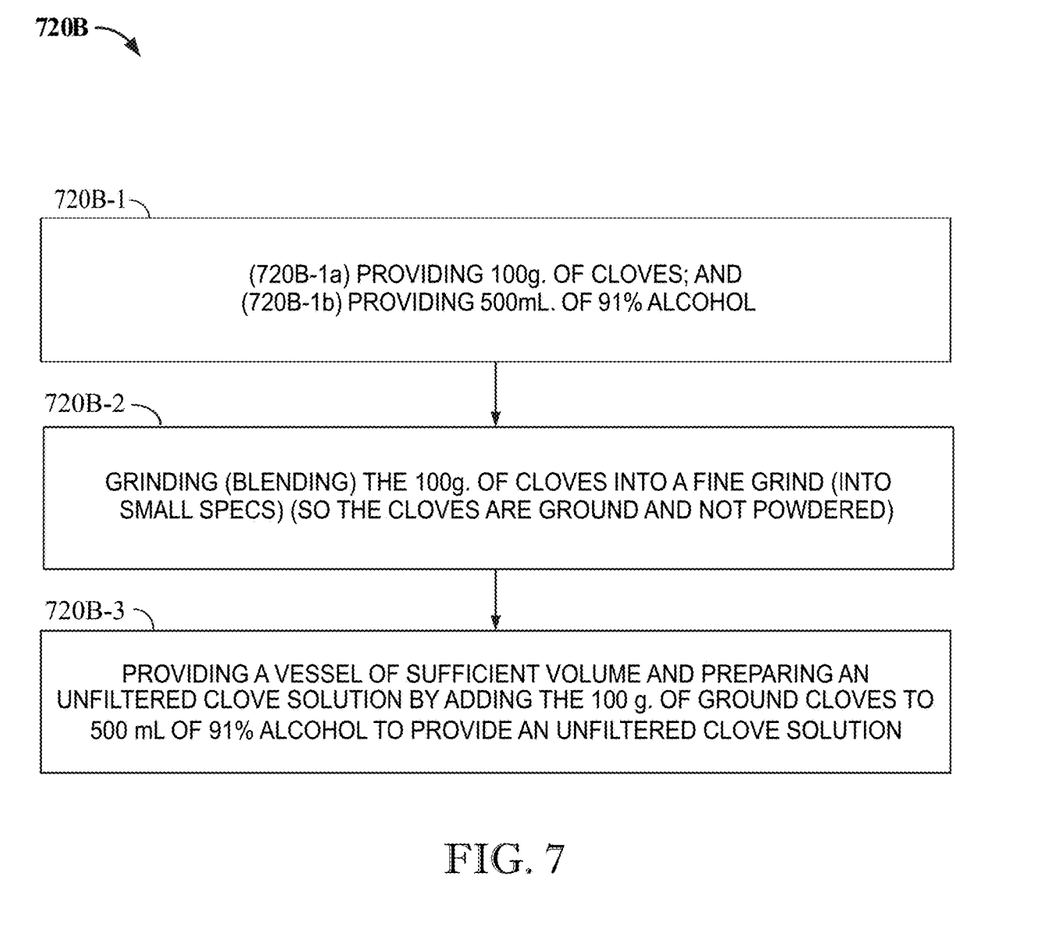
FIG. 7 presents a flow chart of a method in accordance with an illustrative embodiment of the present invention.

Referring now to FIG. 7, a method (720B) for providing a *Clove* component may comprise:
  (720B-1a) providing 100 g. of *Cloves*; and
  (720B-1b) providing 500 mL. of water;
  (720B-2) grinding (blending) the 100 g. of *Cloves* into a fine grind (into all specs) (so the *Cloves* are ground and not powdered); and
  (720B-3) providing a vessel of sufficient volume and preparing an unfiltered *Clove* solution by adding the 100 g. of ground *Cloves* to 500 mL of 91% alcohol to provide an unfiltered *Clove* solution.

Figure 8:
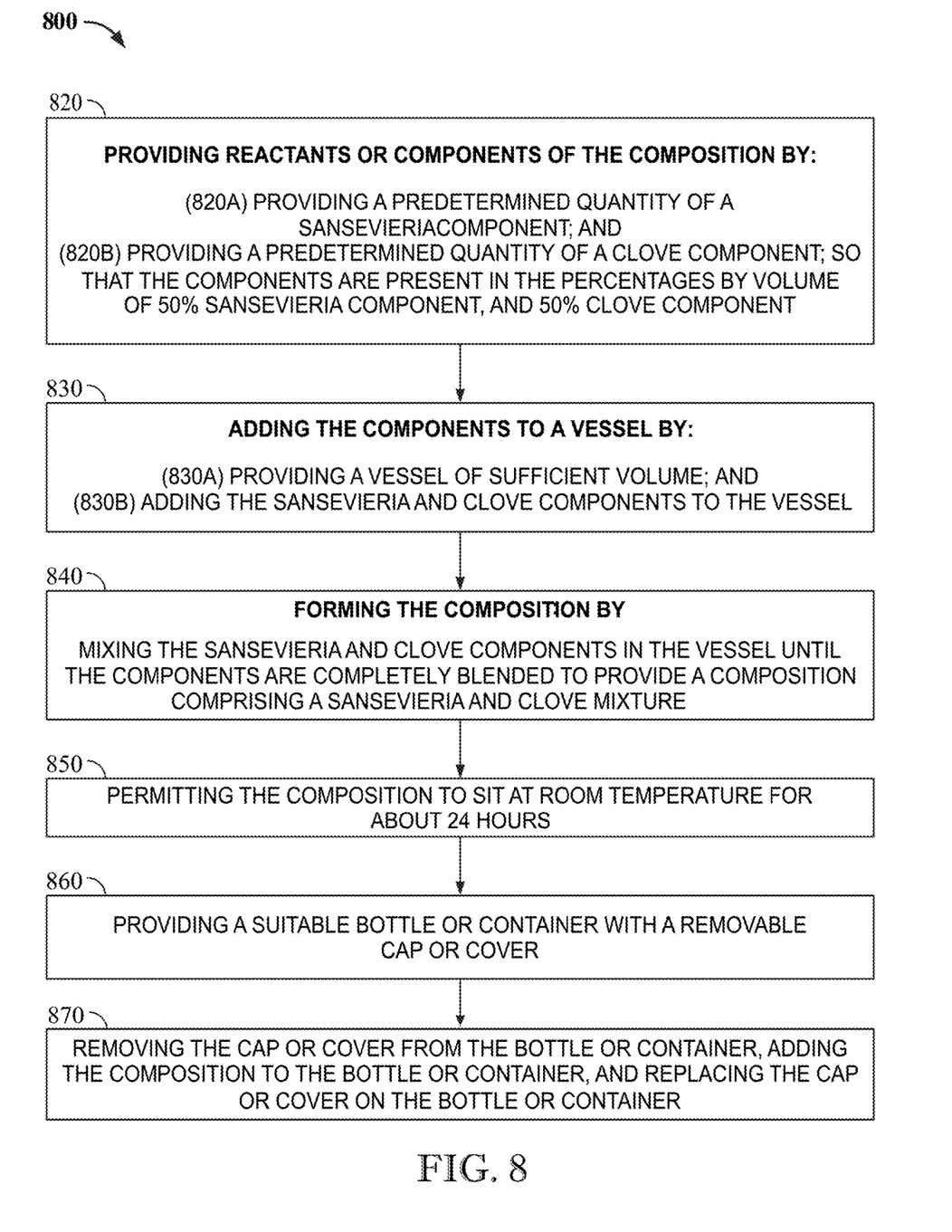
FIG. 8 presents a flow chart of a method in accordance with an illustrative embodiment of the present invention.

Referring now to FIG. 8, a method 800 may comprise the following steps:
  (820) providing reactants or components of the composition by:
  (820A) providing a predetermined quantity of a *Sansevieria* component; and
  (820B) providing a predetermined quantity of a *Clove* component; so that the components are present in the percentages by volume of 50% *Sansevieria* component, and 50% *Clove* component;
  (830C) adding the components to a vessel by:
  (830A) providing a vessel of sufficient volume; and
  (830B) adding the *Sansevieria* and *Clove* components to the vessel;
  (840) forming the composition by mixing the *Sansevieria* and *Clove* components in the vessel until the components are completely blended to provide a composition comprising a *Sansevieria* and *Clove* mixture;
  (850) permitting the composition to sit at room temperature for about 24 hours;
  (860) providing a suitable bottle or container with a removable cap or cover; and
  (870) removing the cap or cover from the bottle or container, adding the composition to the bottle or container, and replacing the cap or cover on the bottle or container.

Figure 9:
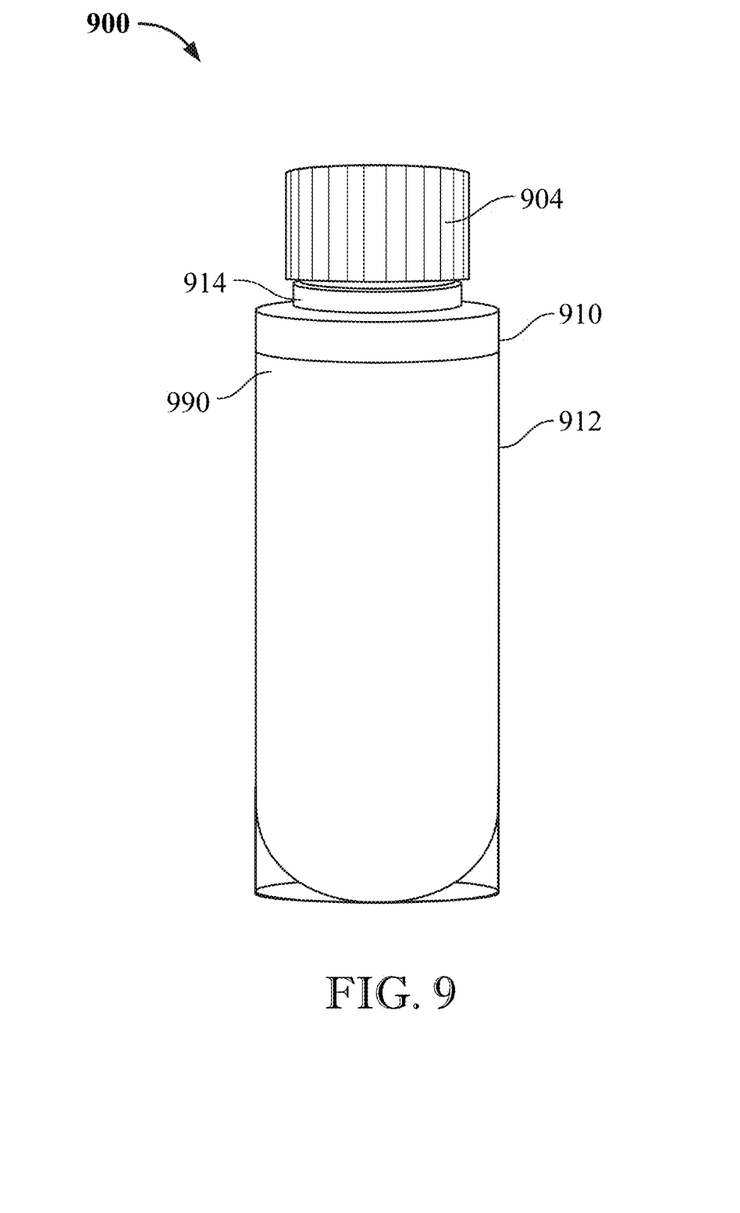
FIG. 9 presents an isometric view of a container with a composition in accordance with an illustrative embodiment of the present invention.

In a third implementation, the composition may be retained and stored in a bottle or container having a cap or cover. As shown at FIG. 9, a nonlimiting example of a bottle or container assembly 900 which may be used to retain and store a composition 990 of the present invention comprises a container 910 having a container body 912 and a container neck 914, which may be an exteriorly threaded neck. The container assembly 900 further comprises a cap or cover 904, which may be an interiorly threaded cap. In some embodiments, the container 910 may configured to hold 1000 mL (1 L) of the composition. However, the container may be any suitable size. For example without limitation, the container may have a smaller volume configured to be portable, purse-size or travel size in accordance with current NTSA guidelines. Further, the container may be made of any suitable material and fabricated by any suitable fabrication process.

In a fourth implementation, the present invention provides a method for treating a medical condition. The method may comprise providing a liquid composition comprising *Sansevieria* and blended *Cloves* and administering the liquid composition. In some embodiments, the liquid composition may comprise equal parts *Sansevieria* and blended *Cloves*. In some embodiments, the liquid composition may comprise by volume 50% of a *Sansevieria* component and 50% of a *Clove* component. In some embodiments, the liquid composition may comprise 100 g. *Sansevieria* and 100 g. blended *Cloves*.

The method further comprises administering or ingesting a predetermined quantity of the liquid composition daily.

In some embodiments, the medical condition comprises cancer.

The method for preventing or treating a cancer may further comprise administering the liquid composition with an additional or supplemental medical treatment. The additional or supplemental medical treatment may be any medical treatment. In some embodiments, the supplemental medical treatment comprises a pharmaceutical drug. Other nonlimiting examples of the additional or supplemental medical treatment may comprise chemotherapy, radiation or the like. For example without limitation, the method may further comprise administering at least one cancer radiation treatment or a plurality of cancer radiation treatments at the discretion of a primary physician or a physician specialist in oncology.

Further, the additional or supplemental medical treatment may comprise any alternative medicine therapy or natural treatment.

Moreover, the medical condition for treatment by the liquid medical treatment composition may be a fungal infection, arthritis, toothache, acne, or other skin conditions. The liquid medical treatment composition may promote wound healing.

In some embodiments, the method further comprises precluding use of the composition by pregnant women, or by women during their menstrual cycle, as the composition may cause hemorrhaging.

Figure 10:
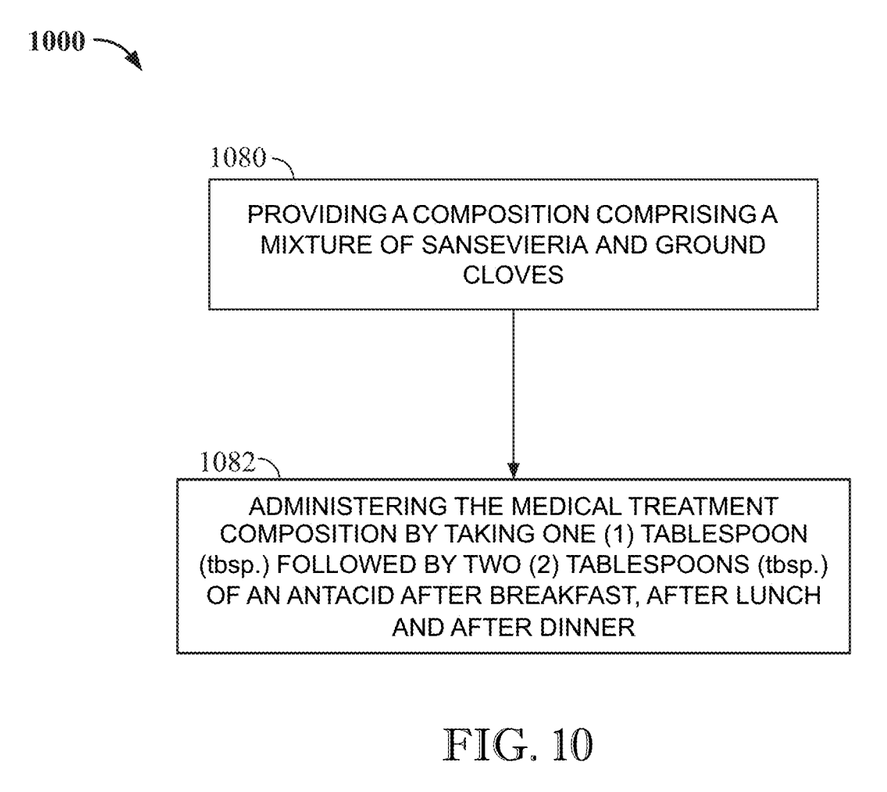
FIG. 10 presents a flow chart of a method in accordance with an illustrative embodiment of the present invention.

Referring now to FIG. 10, a method 1000 for treating a medical condition, comprises:
  (1080) providing a medical treatment composition (best seen at 990 of FIG. 9) comprising a mixture of *Sansevieria* and ground *Clove* as disclosed herein; and (1082) administering the medical treatment composition by taking (ingesting) one tablespoon (1 tbsp.) of the medical treatment composition, followed by taking (ingesting) two tablespoons (2 tbsp.) of a liquid or gel antacid composition after breakfast, after lunch and after dinner.

The antacid composition may be any suitable antacid composition, such as over-the-counter antacid products, or the like.

In a fifth implementation, the present invention provides a method for providing a concentrate of a liquid composition which comprises equal parts *Sansevieria* and blended *Cloves*. The method may include any method steps described herein.

Figure 11:
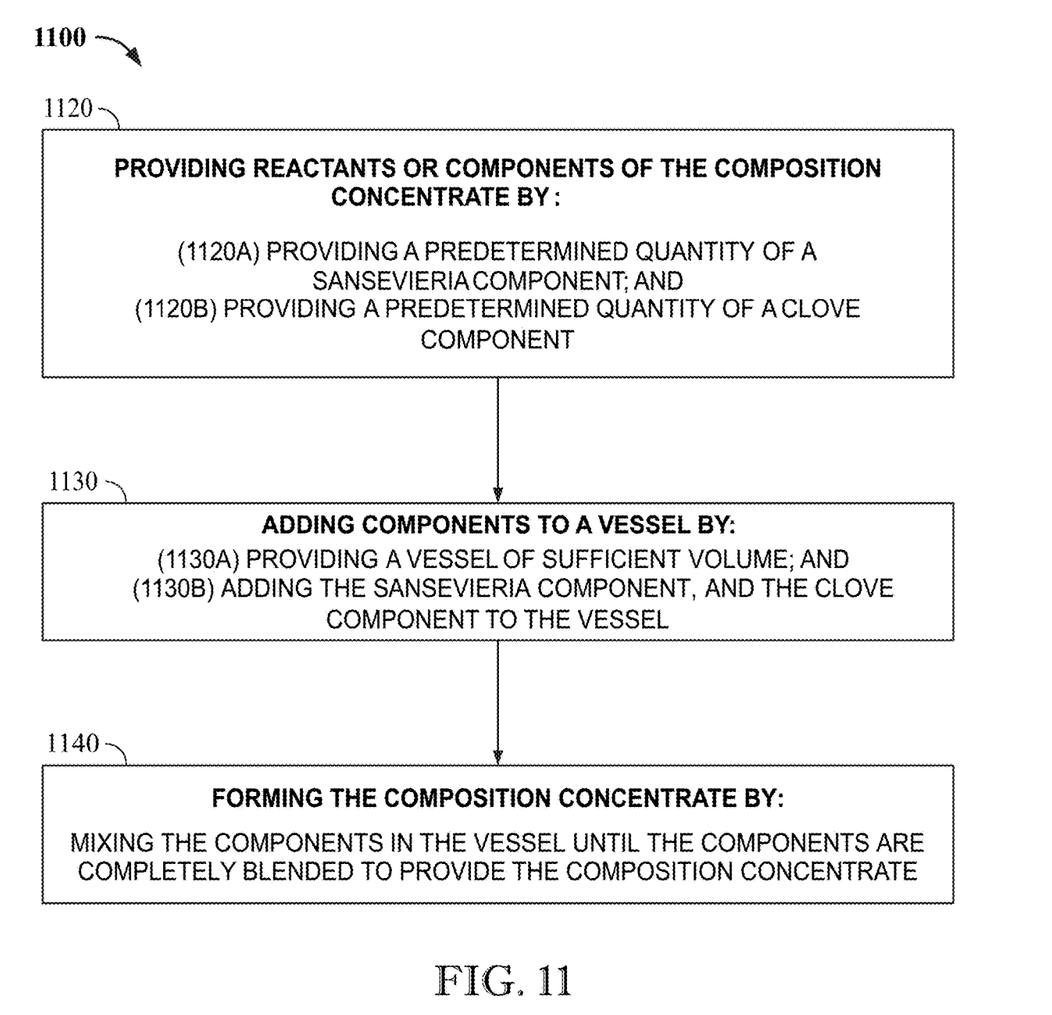
FIG. 11 presents a flow chart of a method in accordance with an illustrative embodiment of the present invention.

Referring now to FIG. 11, a method 1100 for making a composition concentrate may comprise the following steps.
(1120) providing reactants or components of the composition concentrate by:
(1120A) providing a predetermined quantity of a *Sansevieria* component; and
(1120B) providing a predetermined quantity of a *Clove* component;
(1130) adding components to a vessel by:
(1130A) providing a vessel of sufficient volume; and
(1130B) adding the *Sansevieria* component, and the *Clove* component to the vessel;
(1140) forming the composition concentrate by mixing the components in the vessel until the components are completely blended to provide the composition concentrate.

The composition concentrate may include a *Sansevieria* component having a smaller proportion of the water solvent. For example without limitation, a *Sansevieria* component made from about 100 g. of *Sansevieria* may include about 25%-99% of the water (i.e. 25-99% of 500 mL, or between about 125 mL-495 mL). Further, the composition concentrate may include a *Clove* component having a smaller proportion of solvent comprising water, 91% alcohol solvent or a combination thereof. For example without limitation, a *Clove* component made from about 100 g. of *Clove* may include about 25%-99% of the solvent (i.e., 25-99% of the 500 mL of the solvent or between about 125 mL-495 mL). Before use, the concentrate may be "reconstituted" by the addition of a volume of the *Sansevieria* component water solvent and the *Clove* component solvent comprising water, 91% alcohol or a combination thereof—which for a concentrate that includes 100 g. of *Sansevieria*, and 100 g. of *Clove* would be reconstituted to a volume of 1000 mL (1 L).

According to a sixth implementation, the present invention may also provide a method for pest control. The method may comprise providing and reconstituting a concentrate as shown at FIG. 11 and described hereinabove.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A treatment method for treating a medical condition selected from the group consisting of cancer, fungal infection, arthritis, toothache, acne, and wound healing comprising:
providing a liquid medical treatment composition comprising equal parts *Sansevieria* and *Cloves*, prepared by a process comprising:
preparing a *Sansevieria* component comprising a filtered *Sansevieria* solution by:
providing 100 g. of *Sansevieria*;
providing 500 mL of a first solvent comprising water;
adding the predetermined quantity of the first solvent to a vessel, adding the predetermined quantity of *Sansevieria* to the first solvent to provide a *Sansevieria* and water mixture, and filtering the *Sansevieria* and water mixture to provide the *Sansevieria* component;
preparing a *Clove* component comprising an unfiltered *Clove* solution by:
providing 100 g. of *Cloves*;
providing 500 mL of a second solvent selected from room temperature water, 91% alcohol and combinations thereof;
grinding or blending the predetermined quantity of *Cloves* into a fine grind of *Cloves*, into small specks of *Cloves* that are not powdered to provide a predetermined quantity of ground *Cloves*;
providing a second vessel and adding to the second vessel the predetermined quantity of ground *Cloves*, adding the predetermined quantity of the second solvent to provide the *Clove* component;
preparing a *Sansevieria* and ground *Clove* mixture by adding to the *Clove* component the *Sansevieria* component;
blending the *Clove* component and the *Sansevieria* component to create the *Sansevieria* and ground *Clove* mixture; and
permitting the *Sansevieria* and ground *Clove* mixture to sit at room temperature for 24 hours;
whereby a liquid medical treatment composition comprising by volume 5000 of a *Sansevieria* component and 50% of a *Clove* component is provided;
administering a predetermined amount of the composition administering the predetermined amount of the medical treatment composition further comprises:
administering or ingesting one tablespoon (1 tbsp.) of the medical treatment composition;
after administering the composition administering or ingesting two tablespoons (2 tbsp.) of a liquid or gel antacid composition; and
ingesting the predetermined amount of the liquid medical treatment composition daily, wherein the medical condition is cancer.

2. The treatment method of claim 1, wherein the treatment method further comprises administering the medical treatment composition concurrently with an additional or a supplemental medical treatment.

3. The treatment method of claim 2 wherein the additional or supplemental medical treatment comprises a pharmaceutical drug.

4. The treatment method of claim 3 wherein the additional or supplemental medical treatment is selected from chemotherapy, radiation, and combinations thereof.

5. The treatment method of claim 4 wherein the supplemental medical treatment comprises administering at least one cancer radiation treatment or a plurality of cancer radiation treatments at the discretion of a physician.

6. The treatment method of claim 3 wherein the supplemental medical treatment comprises an alternative medicine therapy or a natural treatment.

* * * * *